(12) United States Patent
Kapadia

(10) Patent No.: US 11,116,534 B2
(45) Date of Patent: Sep. 14, 2021

(54) SURGICAL DEVICE FOR GRASPING AND SHEARING

(71) Applicant: Covidien LP, Mansfield, MA (US)

(72) Inventor: Jaimeen Kapadia, Bridgeport, CT (US)

(73) Assignee: COVIDIEN LP, Mansfield, MA (US)

( * ) Notice: Subject to any disclaimer, the term of this patent is extended or adjusted under 35 U.S.C. 154(b) by 928 days.

(21) Appl. No.: 15/102,178

(22) PCT Filed: Oct. 27, 2014

(86) PCT No.: PCT/US2014/062321
§ 371 (c)(1),
(2) Date: Jun. 6, 2016

(87) PCT Pub. No.: WO2015/088660
PCT Pub. Date: Jun. 18, 2015

(65) Prior Publication Data
US 2016/0310156 A1    Oct. 27, 2016

Related U.S. Application Data

(60) Provisional application No. 61/914,644, filed on Dec. 11, 2013.

(51) Int. Cl.
*A61B 17/295* (2006.01)
*B25J 15/02* (2006.01)
(Continued)

(52) U.S. Cl.
CPC ............ *A61B 17/295* (2013.01); *A61B 17/29* (2013.01); *A61B 34/30* (2016.02); *A61B 34/71* (2016.02);
(Continued)

(58) Field of Classification Search
CPC .......... A61B 17/295; A61B 2017/2947; A61B 2017/2938; A61B 2017/2927; A61B 34/71; A61B 2017/00353
See application file for complete search history.

(56) References Cited

U.S. PATENT DOCUMENTS 5,752,644 A    5/1998   Bolanos et al.
6,953,139 B2  10/2005  Milliman et al.
(Continued)

OTHER PUBLICATIONS

International Search Report for (PCT/US2014/062321) date of completion is Jan. 23, 2015 (4 pages).
(Continued)

*Primary Examiner* — Thomas McEvoy
(74) *Attorney, Agent, or Firm* — Carter, DeLuca & Farrell LLP

(57) ABSTRACT

The present disclosure relates to a surgical device including a body portion and an end effector. The body portion defines a longitudinal axis. The end effector is disposed adjacent a distal end of the body portion and includes first and second jaw members. At least one jaw member is pivotable with respect to the other jaw member between open and approximated positions along a first plane. Each jaw member is independently movable with respect to the other jaw member between a first position where the jaw members are aligned with the longitudinal axis and a second position where at least one jaw member is disposed at an angle with respect to the longitudinal axis and with respect to the first plane.

16 Claims, 12 Drawing Sheets

(51) Int. Cl.
*A61B 34/00* (2016.01)
*A61B 17/29* (2006.01)
*A61B 34/30* (2016.01)

(52) U.S. Cl.
CPC ..... *B25J 15/0233* (2013.01); *A61B 2034/305* (2016.02)

(56) References Cited

U.S. PATENT DOCUMENTS

| | | |
|---|---|---|
| 6,969,385 B2 | 11/2005 | Moreyra |
| 2003/0208186 A1 | 11/2003 | Moreyra |
| 2007/0179525 A1 | 8/2007 | Frecker et al. |
| 2008/0046122 A1 | 2/2008 | Manzo et al. |
| 2008/0119870 A1 | 5/2008 | Williams |
| 2010/0168787 A1* | 7/2010 | Surti ............... A61B 17/29 606/205 |
| 2010/0191251 A1 | 7/2010 | Scott et al. |
| 2011/0238064 A1 | 9/2011 | Williams |
| 2012/0116416 A1 | 5/2012 | Neff et al. |
| 2012/0209305 A1 | 8/2012 | Deodhar et al. |

OTHER PUBLICATIONS

Chinese Office Action issued in corresponding Chinese Application No. 201480067489.2 dated Feb. 1, 2018.
Extended European Search Report issued in corresponding European Application No. 14870303.6 dated Jul. 21, 2017.
Chinese Office Action issued in Chinese Application No. 201480067489.2 dated Oct. 22, 2018.

\* cited by examiner

SURGICAL DEVICE FOR GRASPING AND SHEARING

CROSS-REFERENCE TO RELATED APPLICATIONS

This application is a U.S. National Stage Application filed under 35 U.S.C. § 371(a) of International Patent Application No. PCT/US2014/062321, filed Oct. 27, 2014, which claims benefit of U.S. Provisional Patent Application No. 61/914,644, filed Dec. 11, 2013, the entire disclosure of each of which is incorporated by reference herein.

BACKGROUND

1. Technical Field

The present disclosure relates to surgical devices and/or systems, and their methods of use. More specifically, the present disclosure relates to a single surgical device and/or system capable of both grasping tissue and shearing tissue.

2. Background of Related Art

One type of surgical device was a linear clamping, cutting and stapling device. Such a device was used in surgical procedures to resect a cancerous or anomalous tissue from a gastro-intestinal tract, for example. Conventional linear clamping, cutting and stapling instruments included a pair of jaw members, which clamped the open ends of the colon closed, for example. In this device, the jaw members pivoted with regard to each other, e.g., one jaw member pivoted toward and away from the other jaw member. Additionally, in some devices, the jaw members articulated together with regard to the shaft.

Another type of surgical device was a shearing device. Shearing instruments were generally scissor-like devices that were used in surgical procedures to cut tissue. Conventional shearing instruments typically included a pair of jaw members that opened and closed in a scissors-like fashion to cut tissue.

Many surgical procedures often required the functions of both clamping and cutting. In such procedures, two separate surgical instruments (i.e., a clamping device and a shearing device) were used to accomplish these two functions. However, the amount of operating space in and/or around the patient was often limited and the size of the incision in the patient's skin was kept small to minimize healing time, lessen scarring, and reduce blood loss. This made it cumbersome and difficult to use and switch between the two separate devices.

There is therefore a need for a single surgical instrument that can both clamp and cut tissue.

SUMMARY

The present disclosure relates to a single surgical device having jaw members that both clamp and cut tissue depending on the direction in which the jaw members are moved. In some instances, a first jaw member may be pivotable away from and towards a second jaw member to grab tissue. At least one of jaw members may also be movable in a different direction from the pivoting to cut tissue. In other instances, the opposite may occur as the first jaw member is pivoted to cut tissue and at least one jaw member is moved in a different direction to grab tissue.

A surgical device may include a body portion and an end effector. The body portion defines a longitudinal axis. The end effector may be disposed adjacent a distal end of the body portion and includes a first jaw member and a second jaw member. At least one jaw member may be pivotable with respect to the other jaw member between open and approximated positions along a first plane. Each jaw member may be independently movable with respect to the other jaw member between a first position where the jaw members are aligned with the longitudinal axis and a second position where at least one jaw member is disposed at an angle with respect to the longitudinal axis and with respect to the first plane.

In some disclosed embodiments, each jaw member may be pivotable with respect to the other jaw member. Each jaw member may be independently pivotable with respect to the other jaw member.

Further, the present disclosure includes embodiments where the first jaw member may be movable in a second plane toward its second position, and the second jaw member may be movable in the second plane toward its second position. The first jaw member and the second jaw member may be concurrently movable in opposite directions from each other within the second plane.

The jaw members may be disposed at an angle with respect to one another when the jaw members are in the second position. Each jaw member may be disposed at an angle with respect to the longitudinal axis and with respect to the first plane when the jaw member is disposed in its second position.

The end effector may include a first pulley and a second pulley associated with each jaw member. Rotation of the first pulley may cause the respective jaw member to move within the first plane, and rotation of the second pulley may cause the respective jaw member to within the second plane. The end effector may include four idler pulleys associated with each jaw member. A first set of four idler pulleys may be located adjacent a lateral wall of the body portion and may be associated with one of the jaw members, and a second set of four idler pulleys may be located laterally outward of the first set of four idler pulleys and may be associated with the other of the jaw members. It is further disclosed that the end effector may include a first cable associated with the first pulley of the first jaw member, a second cable associated with the second pulley of the first jaw member, a third cable associated with the first pulley of the second jaw member, and a fourth cable associated with the second pulley of the second jaw member. At least one of proximal and distal movement of a cable may result in rotation of its respective pulley.

The end effector may include a first pulley associated with each jaw member. Rotation of the first pulley may cause the respective jaw member to move within the first plane. The first pulley associated with the first jaw member may have a different diameter than the first pulley associated with the second jaw member. The diameter of the first pulley associated with the first jaw member may be between about 3 mm and about 4 mm.

A robotic medical system may include a master station, a slave station and a controller. The master station may include an input device. The slave station may include a surgical instrument including a body portion and an end effector. The body portion may define a longitudinal axis. The end effector may be disposed adjacent a distal end of the body portion and may include a first jaw member and a second jaw member. At least one jaw member may be pivotable with respect to the other jaw member between open and approximated positions along a first plane. Each jaw member may be independently movable with respect to the other jaw member between a first position where the jaw members are aligned with the longitudinal axis and a second position where the jaw members are disposed at an angle with respect to the longitudinal axis and with respect to the first plane. The controller may be coupled between the master station and the slave station and may be configured for receiving a command from the input device and for controlling movement of the surgical instrument.

Each jaw member may be independently pivotable with respect to the other jaw member. The first jaw member may be movable in a second plane toward its second position, and the second jaw member may be concurrently movable with the first jaw member in an opposite direction from the first jaw member in the second plane toward its second position.

The end effector may include a first pulley and a second pulley associated with each jaw member. Rotation of the first pulley may cause the respective jaw member to move within the first plane, and rotation of the second pulley may cause the respective jaw member to within the second plane.

In some instances, a first jaw member at an end effector of a surgical device may be pivoted with respect to a second jaw member at the end effector between a first open position and an approximated position along a first plane. At least one of the jaw members may be moved while in the approximated position between the approximated position and a second open position along a second plane non-parallel to the first plane.

In some instances, an object between the jaw members may be grabbed responsive to pivoting the first jaw member from the first open position to the approximated position. The object may be cut responsive to moving the at least one jaw member from the second open position to the approximated position when the object is between the jaw members in the second open position.

In other instances, an object between the jaw members may be cut responsive to pivoting the first jaw member from the first open position to the approximated position. The object may be grabbed responsive to moving the at least one jaw member from the second open position to the approximated position when the object is between the jaw members in the second open position.

A longitudinal axis may be defined along a body portion of the surgical device to which the end effector is coupled. Each jaw member may be independently moved between the approximated position, where the jaw members are aligned with the longitudinal axis, and at least one open position, where each jaw member is disposed at angle with respect to the longitudinal axis and with respect to the first plane.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1A:
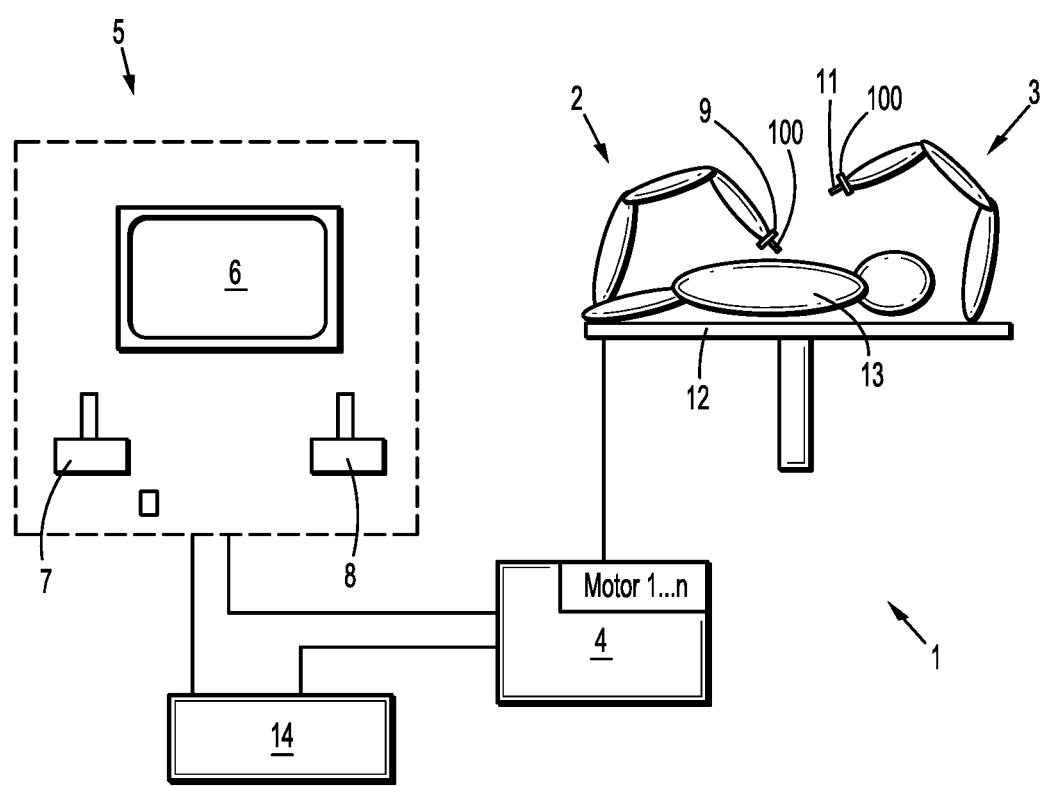
FIG. 1A is a schematic illustration of a medical work station and operating console in accordance with the present disclosure.

Embodiments of the presently disclosed surgical devices and robotic medical systems are described in detail with reference to the drawings, in which like reference numerals designate identical or corresponding elements in each of the several views. As used herein the term "distal" refers to that portion of the surgical device, or component thereof, farther from the user, while the term "proximal" refers to that portion of the surgical device, or component thereof, closer to the user.

Figure 1B:
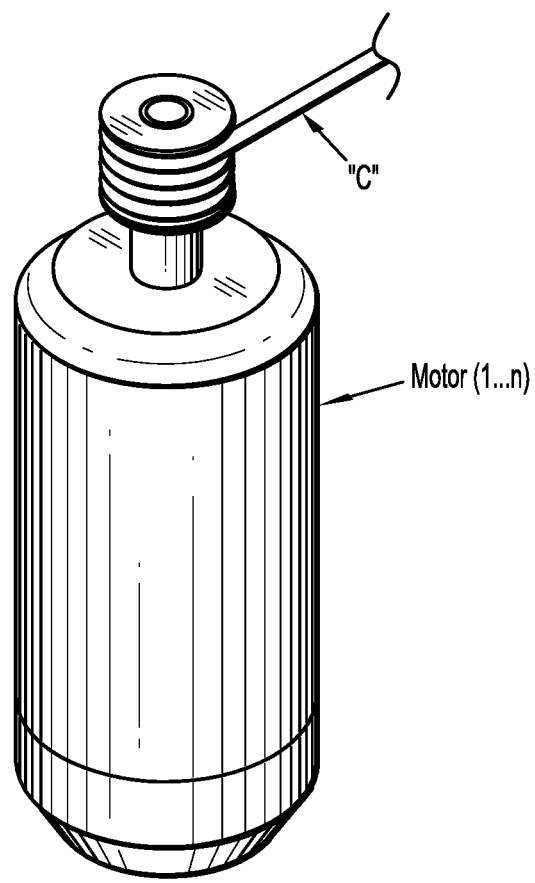
FIG. 1B is a schematic, perspective view of a motor of a control device of the medical work station of FIG. 1A

Referring initially to FIG. 1, a medical work station is shown generally as work station 1 and generally includes a plurality of robot arms 2, 3, a control device 4, and an operating console 5 coupled with control device 4. Operating console 5 includes a display device 6, which is set up in particular to display three-dimensional images. Manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an attaching device 9, 10, to which may be attached, for example surgical device 100, in accordance with any one of several embodiments disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, their attaching devices 9, 10 and thus surgical device 100 execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of surgical device 100. Medical work station 1 may also include more than two robot arms 2, 3, the one or the additional robot arms likewise being connected to control device 4 and being telemanipulable by means of operating console 5. A medical instrument (e.g., surgical device 100) may also be attached to the additional robot arm.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (Motor 1 . . . n) with each motor configured to wind-up or let out a length of a cable "C" extending through each robot arm 2, 3 to surgical device 100. In use, as cables "C" are wound-up and let out, cables "C" effect operation and/or movement of each surgical device 100. It is contemplated that control device 4 coordinates the activation of the various motors (Motor 1 . . . n) to coordinate a winding-up or letting out a length of a respective cable "C" in order to coordinate an operation and/or movement of a respective surgical device 100.

Additionally, while FIG. 1 illustrates surgical device 100 as being part of robotic work station 1, the present disclosure includes surgical device 100 as being included on a handheld surgical instrument, such as the endoscopic surgical stapling instruments described in detail in commonly-owned U.S. Pat. No. 6,953,139 to Milliman et al., the entire contents of which are hereby incorporated by reference herein. Surgical device 100 of the present disclosure may also be part of a loading unit for use with a surgical stapling instrument, such as the loading units disclosed in commonly-owned U.S. Pat. No. 5,752,644 to Bolanos et al., the entire contents of which are hereby incorporated by reference herein.

As illustrated in FIGS. 2-10 surgical device 100 of the present disclosure includes a body portion 200 and an end effector 300 operatively disposed at a distal end of body portion 200. Body portion 200 defines a longitudinal axis A-A extending therethrough. End effector 300 includes a first jaw member 400, and a second jaw member 500. As discussed in further detail below, each jaw member 400 and 500 is independently movable with respect to the other jaw member and with respect to body portion 200 within a first plane "B" (see FIG. 6) and within a second plane "C" (see FIG. 8). Moreover, surgical device 100 is usable for clamping, grasping or dissecting tissue when at least one jaw member 400, 500 moves within the first plane "B," and surgical device 100 is usable for shearing, cutting or dissecting tissue when at least one jaw member 400, 500 moves within the second plane "C."

Figure 2:
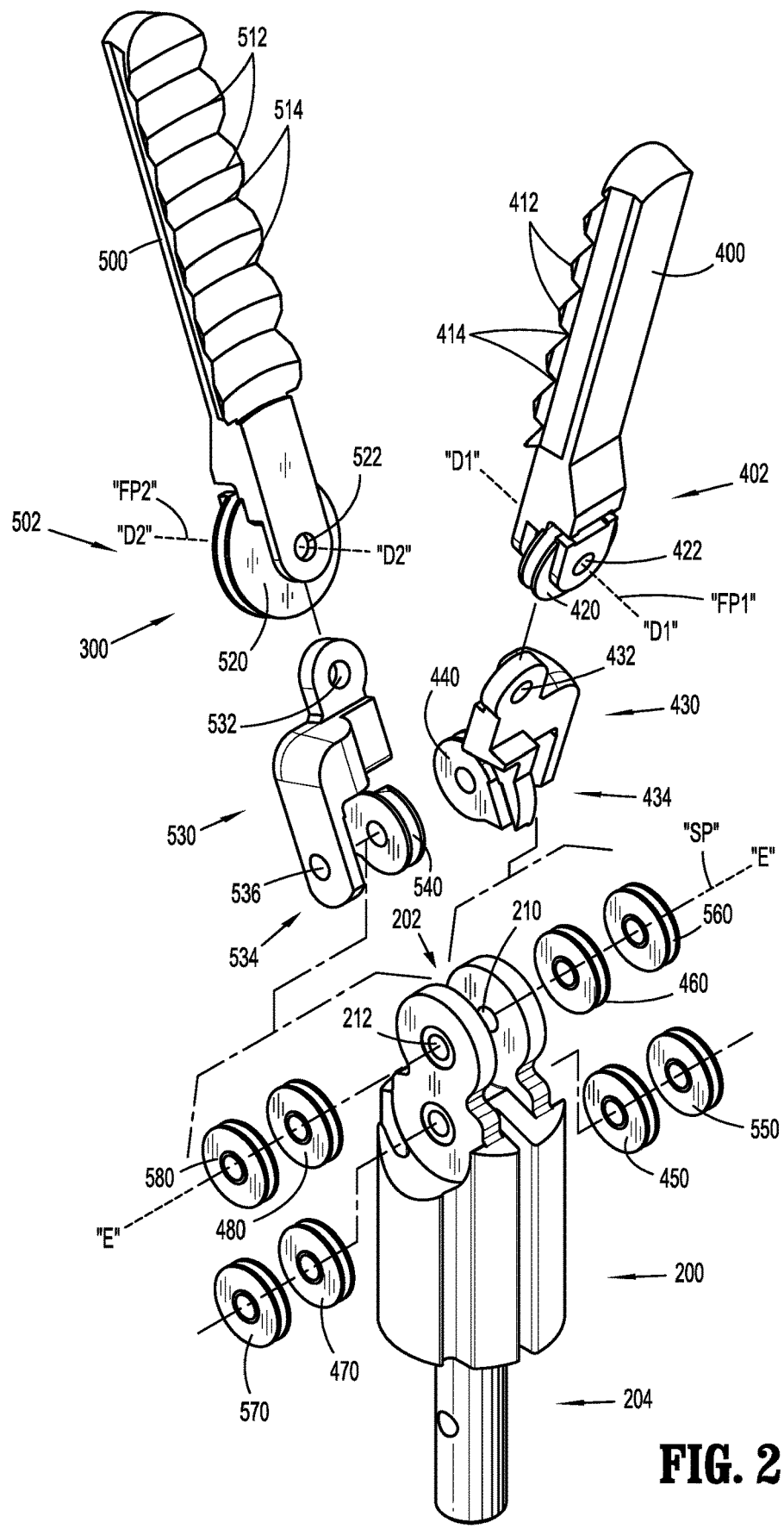
FIG. 2 is a perspective view, with parts separated, of the surgical device of FIG. 1.
Figure 3:
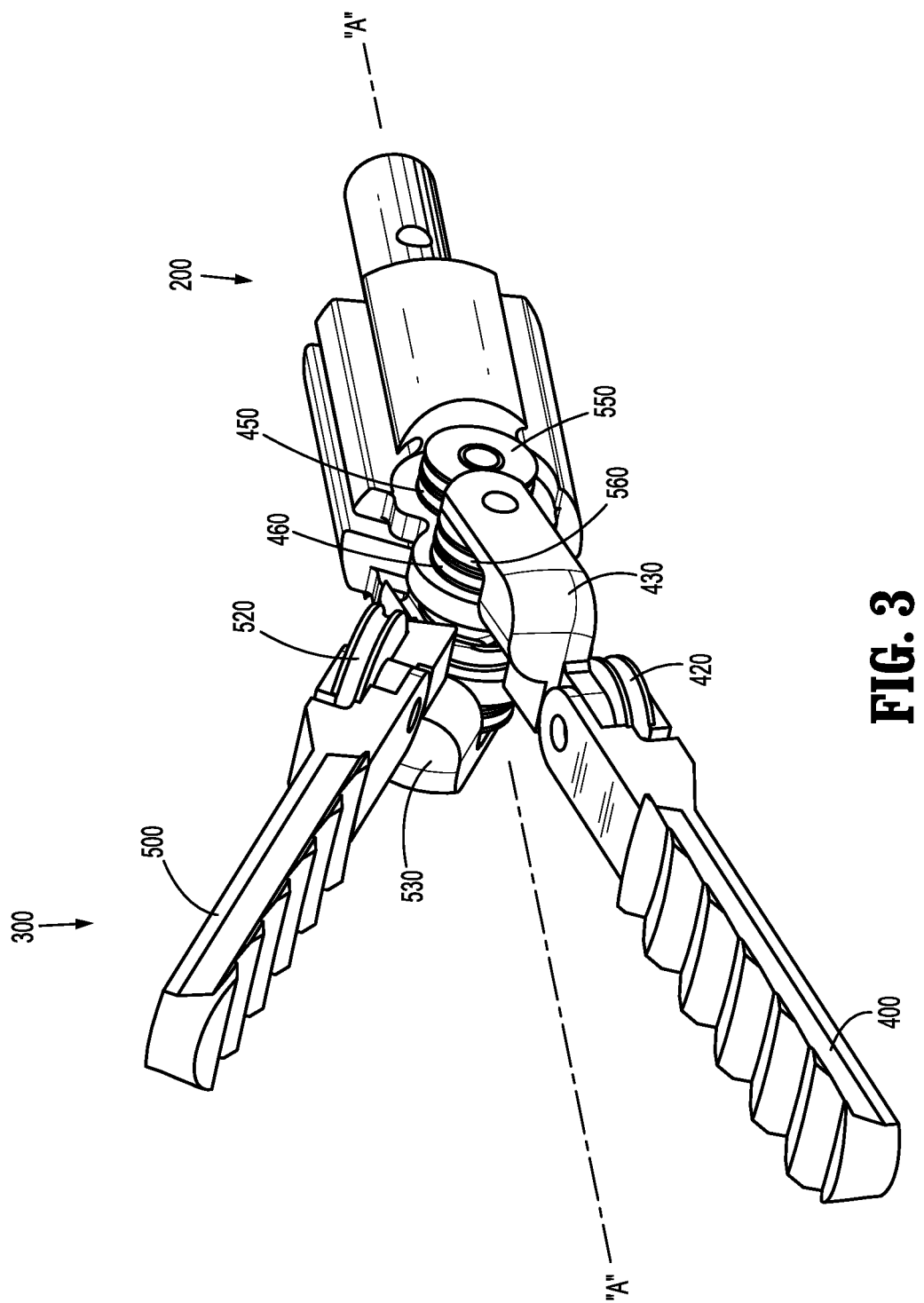
FIGS. 3 and 4 are perspective views of the surgical device of the present disclosure illustrating jaw members in a first open position and a second open position along a first plane.
Figure 9:
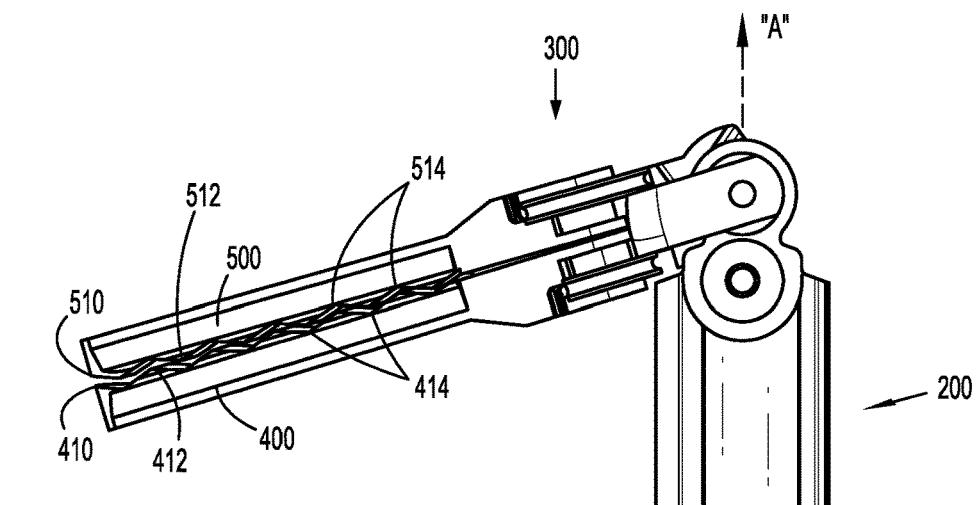
FIG. 9 is a top view of the surgical device of the present disclosure illustrating the jaw members in a closed position and in an articulated position.
Figure 8:
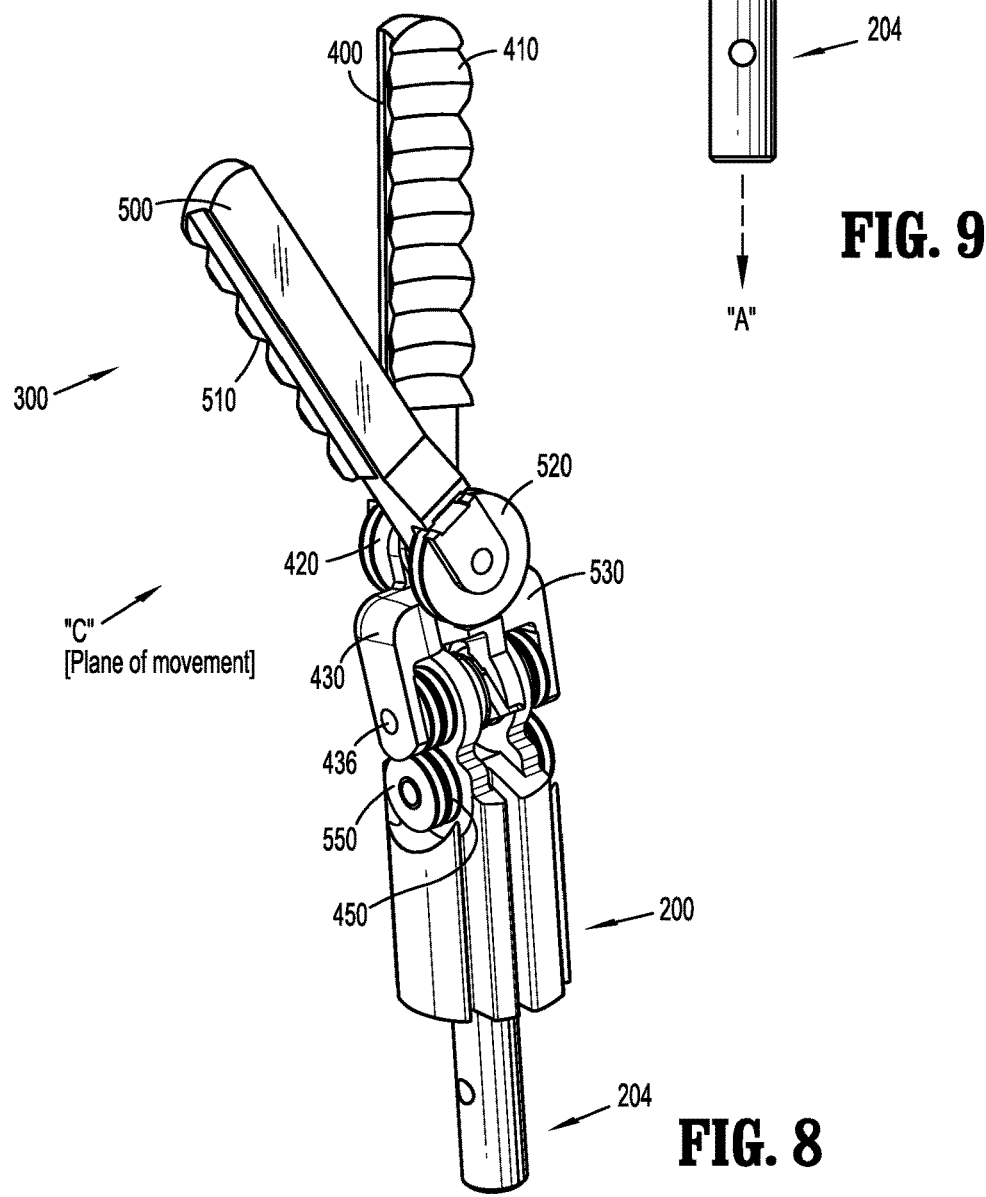
FIG. 8 is another perspective view of the surgical device of the present disclosure illustrating the jaw members along the second plane and including one jaw member in an open or angled position and the other jaw member in a closed or aligned position.

With reference to FIGS. 2 and 9, first jaw member 400 includes a tissue contacting surface 410 including a series of teeth defined by a plurality of peaks 412 and valleys 414. Additionally, second jaw member 500 includes a tissue contacting surface 510 including a series of teeth defined by a plurality of peaks 512 and valleys 514. Additionally, and as shown in FIG. 9, for example, when first jaw member 400 and second jaw member 500 are approximated, peaks 412 of first jaw member 400 are opposite valleys 514 (i.e., between adjacent peaks 512) of second jaw member 500, and valleys 414 of first jaw member 400 are opposite peaks 512 (i.e., between adjacent valleys 514) of second jaw member 500. It is envisioned that this arrangement facilitates grasping tissue therebetween and allows one jaw member to slide (i.e., move within the second plane "C") relative to the other jaw member. It is contemplated that each peak 412, 512 and valley 414, 514 has an arcuate or curved profile.

With continued reference to FIG. 2, for example, a proximal portion 402 of first jaw member 400 includes a pitch pulley or a first pulley 420 disposed thereon. First jaw member 400 is configured to mechanically engage a first jaw mount 430, e.g., via a pinned connection between a proximal aperture 422 of first jaw member 400 and a distal aperture 432 of first jaw mount 430. This pivotable connection, between first jaw member 400 and first jaw mount 430, defines a first pivot axis "D1" which enables first jaw member 400 to move within the second plane "C," e.g., to shear tissue.

A proximal portion 502 of second jaw member 500 includes a pitch pulley or a first pulley 520 disposed thereon. Second jaw member 500 is configured to mechanically engage a second jaw mount 530, e.g., via a pinned connection between a proximal aperture 522 of second jaw member 500 and a distal aperture 532 of second jaw mount 530. This pivotable connection, between second jaw member 500 and second jaw mount 530, defines a second pivot axis "D2" which enables second jaw member 500 to move within the second plane "C," e.g., to shear tissue.

Moreover, surgical device 100 is usable to shear or dissect tissue, for instance, when first jaw member 400 and second jaw member 500 are moved in opposite directions, about pivot axes "D1" or "D2," along the second plane "C." Further, when first jaw member 400 and second jaw member 500 are moved in the same direction, about pivot axes "D1" or "D2," along the second plane "C," end effector 300 is moved toward an articulated position with respect to body portion 200.

Additionally, and with continued reference to FIG. 2, a proximal portion 434 of first jaw mount 430 includes a grab pulley or a second pulley 440 disposed thereon. Second pulley 440 is configured to mechanically engage a distal portion or clevis 202 of body portion 200, e.g., via a pinned connection between a proximal aperture 436 (FIG. 8) of first jaw mount 430 and a first aperture 210 of body portion 200. This pivotable connection, between first jaw mount 430 and body portion 200, defines a common pivot axis "E" which enables first jaw mount 430, and thus first jaw member 400, to move within the first plane "B,", e.g., to clamp tissue.

A proximal portion 534 of second jaw mount 530 includes a grab pulley or a second pulley 540 disposed thereon. Second pulley 540 is configured to mechanically engage distal portion or clevis 202 of body portion 200, e.g., via a pinned connection between a proximal aperture 536 of second jaw mount 530 and a second aperture 212 of body portion 200. This pivotable connection, between second jaw mount 530 and body portion 200, is disposed on common pivot axis "E," and enables second jaw mount 530, and thus second jaw member 500, to move within the first plane "B," e.g., to clamp tissue.

Moreover, surgical device 100 is usable to clamp or dissect tissue, for instance, when first jaw member 400 and second jaw member 500 are moved in opposite directions, while axially aligned with one another or in a juxtaposed position with one another, within the first plane "B," and about common pivot axis "E." When first jaw member 400 and second jaw member 500 are moved in the same direction within the first plane "B," end effector 300 is moved toward an articulated position with respect to body portion 200 (see FIG. 9). In view of the foregoing, first plane "B" may be defined by longitudinal axis "A-A" and axes "D1" and "D2." Also, second plane "C" may be defined by longitudinal axis "A-A" and common axis "E."

Figure 4:
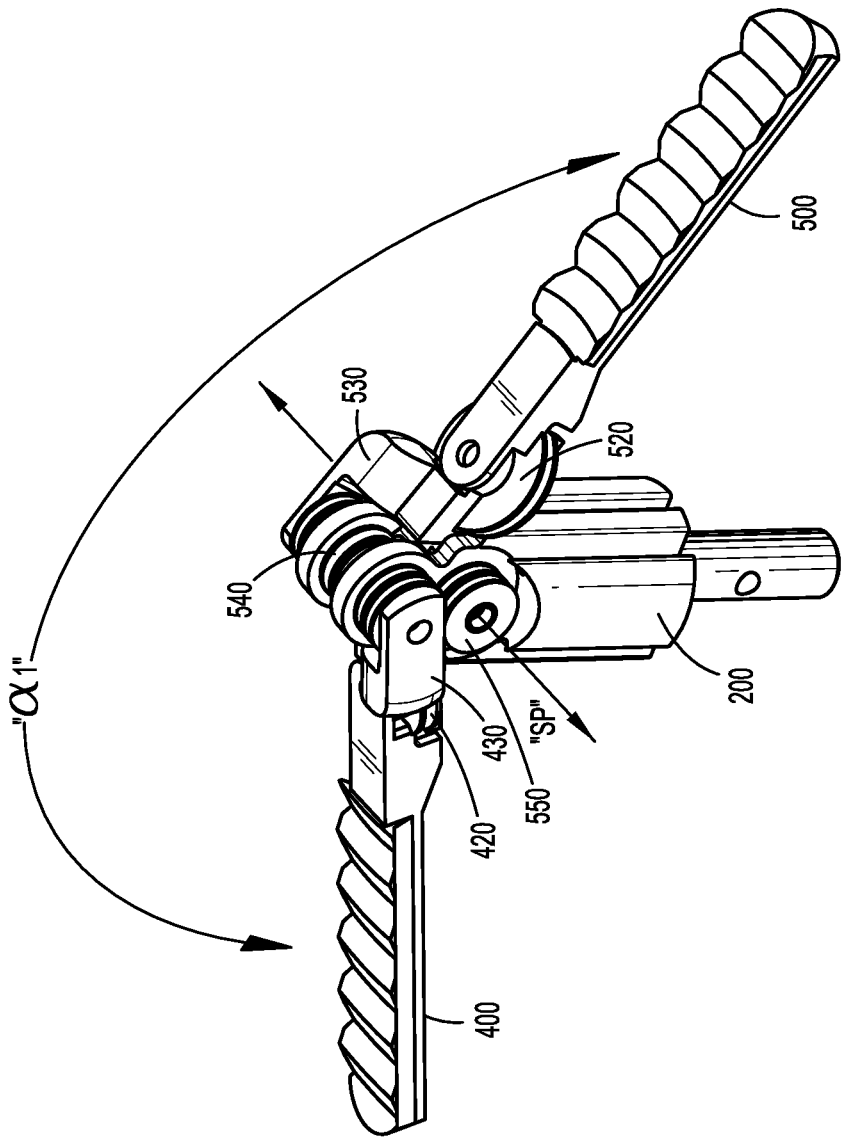

It is envisioned that when first jaw member 400 and second jaw member 500 are in their fully open positions, pivoted about common axis "E" within the first plane "B," they form an angle "α1" of about 220° therebetween (as illustrated in FIG. 4, for example).

With continued reference to FIG. 2, for example, distal portion 202 of body portion 200 includes a first, inner pair of proximal and distal idler pulleys 450 and 460 on a first lateral side thereof, and a second, inner pair of proximal and distal idler pulleys 470 and 480 on a second lateral side thereof. Inner idler pulleys 450, 460, 470 and 480 are rotatable with respect to distal portion 202 of body portion, e.g., via a pinned connection therebetween, and are associated with first jaw member 400 via at least one cable, as described below.

Distal portion 202 of body portion 200 also includes a first, outer pair of proximal and distal idler pulleys 550 and 560 on a first lateral side thereof, and a second, outer pair of proximal and distal idler pulleys 570 and 580 on a second lateral side thereof. Outer idler pulleys 550, 560, 570 and 580 are rotatable with respect to distal portion 202 of body portion, e.g., via a pinned connection therebetween, and are associated with second jaw member 500 via at least one cable, as described below.

Figure 7:
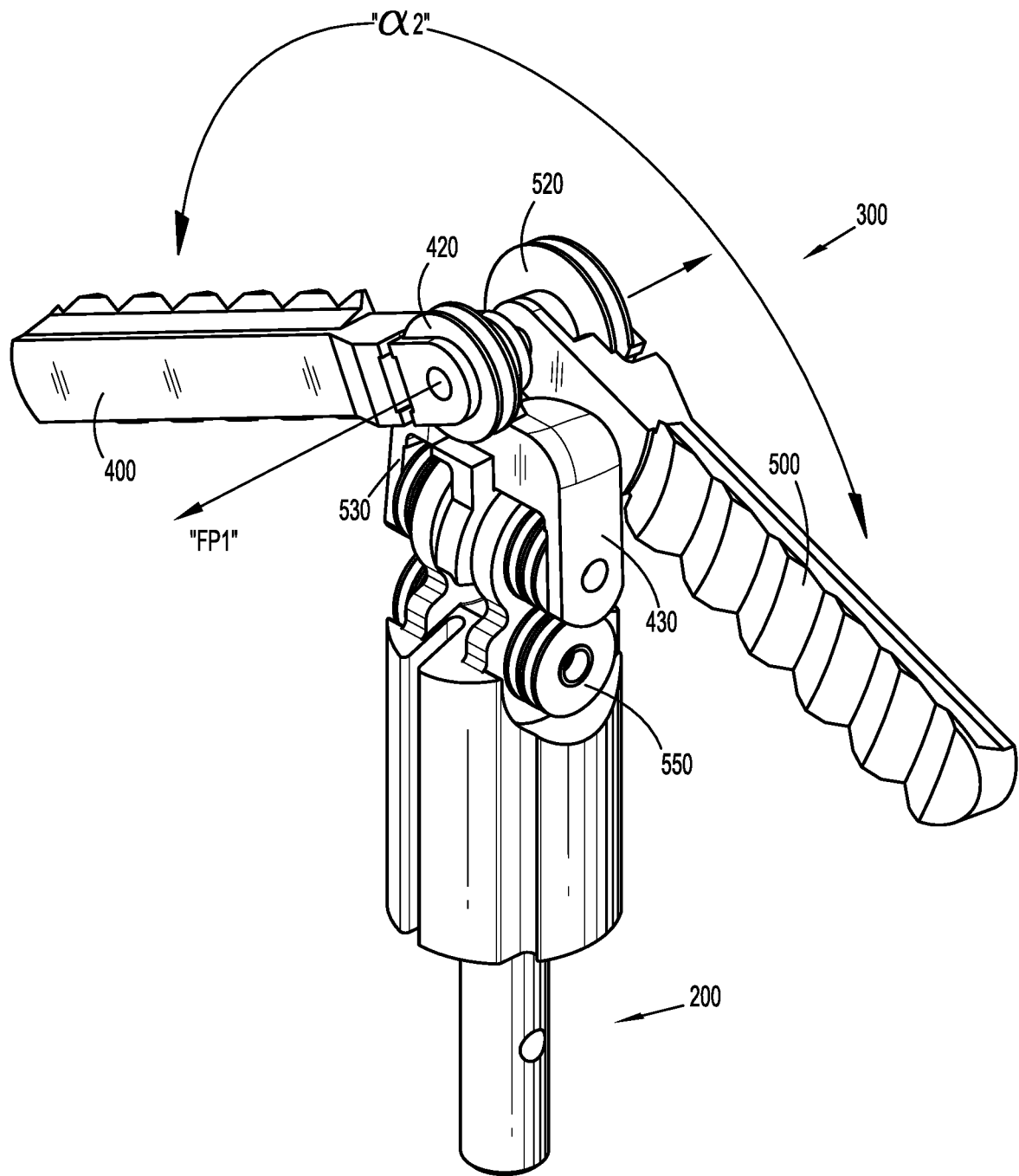
FIG. 7 is a perspective view of the surgical device of the present disclosure illustrating the jaw members in an open position along a second plane.

It is envisioned that when first jaw member 400 and second jaw member 500 are in their fully open positions along the second plane "C," they form an angle "α2" of about 240° therebetween (as illustrated in FIG. 7, for example).

Referring now to FIGS. 2-5, 7, 8 and 10, for example, surgical device 100 includes four cables (FIG. 5); two cables are configured for use with each jaw member 400, 500. A first pitch cable 600 extends from a proximal portion 204 (FIG. 2) of body portion 200 into mechanical cooperation with first, inner pair of proximal and distal idler pulleys 450 and 460 (FIG. 2; e.g., such that cable 600 extends between proximal idler pulley 450 and distal idler pulley 460), around first pulley 420 of first jaw member 400, and into mechanical cooperation with second, inner pair of proximal and distal idler pulleys 470 and 480 (e.g., such that cable 600 extends between proximal idler pulley 470 and distal idler pulley 480). Proximal and/or distal movement of first pitch cable 600 with respect to body portion 200 causes first jaw member 400 to move about a first pulley axis "FP1" (or axis "D1") of first jaw member 400 (FIG. 7) and within the second plane "C," e.g., to shear or dissect tissue.

Figure 5:
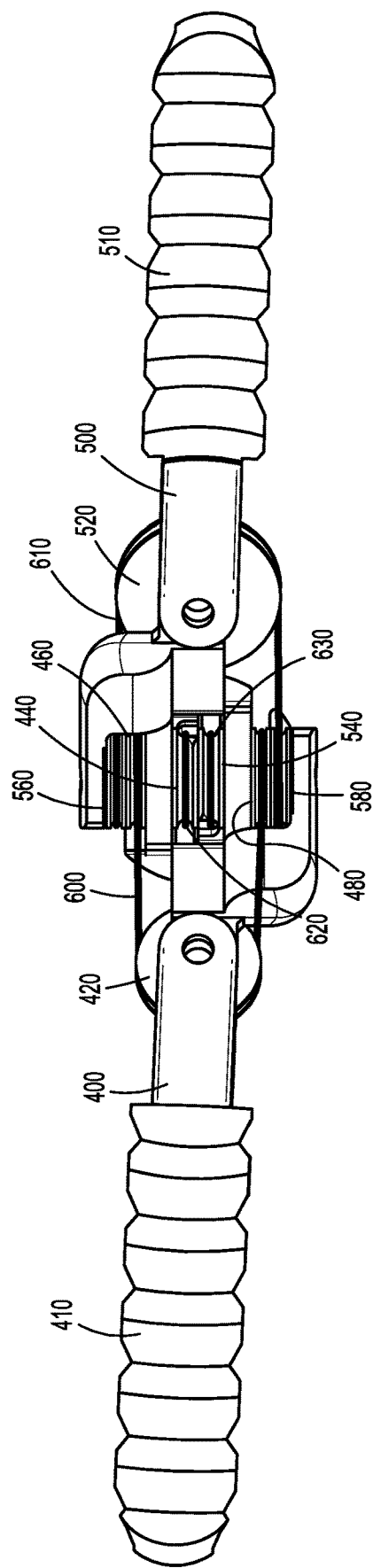
FIG. 5 is a proximal-facing view of the surgical device with the jaw members in an open position while in the first plane.
Figure 10:
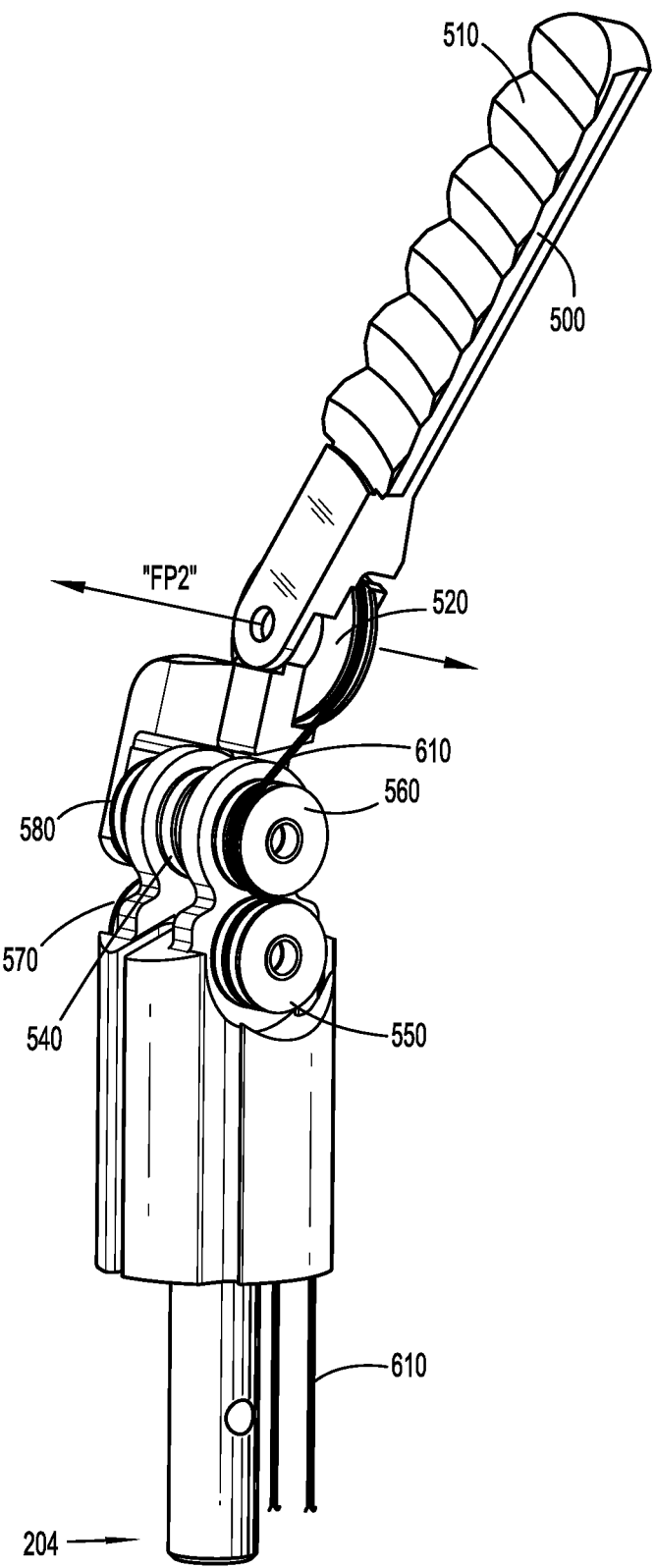
FIG. 10 is a perspective view of one of the jaw members of the surgical device in an open or angled position.

With continued reference to FIG. 5 and with additional reference to FIG. 10, for example, a second pitch cable 610 extends from proximal portion 204 of body portion 200 into mechanical cooperation with first, outer pair of proximal and distal idler pulleys 550 and 560 (e.g., such that cable 610 extends between proximal idler pulley 550 and distal idler pulley 560), around first pulley 520 of second jaw member 500, and into mechanical engagement with second, outer pair of proximal and distal idler pulleys 570 and 580 (e.g., such that cable 610 extends between proximal idler pulley 570 and distal idler pulley 580). Proximal and/or distal movement of second pitch cable 610 with respect to body portion 200 causes second jaw member 500 to move about a first pulley axis "FP2" (or axis "D2") of second jaw member 500 and within the second plane "C," e.g., to also shear or dissect tissue.

With continued reference to FIG. 5, for example, a first grab cable 620 extends from proximal portion 204 of body portion 200 and around second pulley 440 of first jaw mount 430 (for clarity, only a distal portion of first grab cable 620 is illustrated). A second grab cable 630 extends from proximal portion 204 of body portion 200 and around second pulley 540 of second jaw mount 530 (for clarity, only a distal portion of second grab cable 630 is illustrated).

Figure 4A:
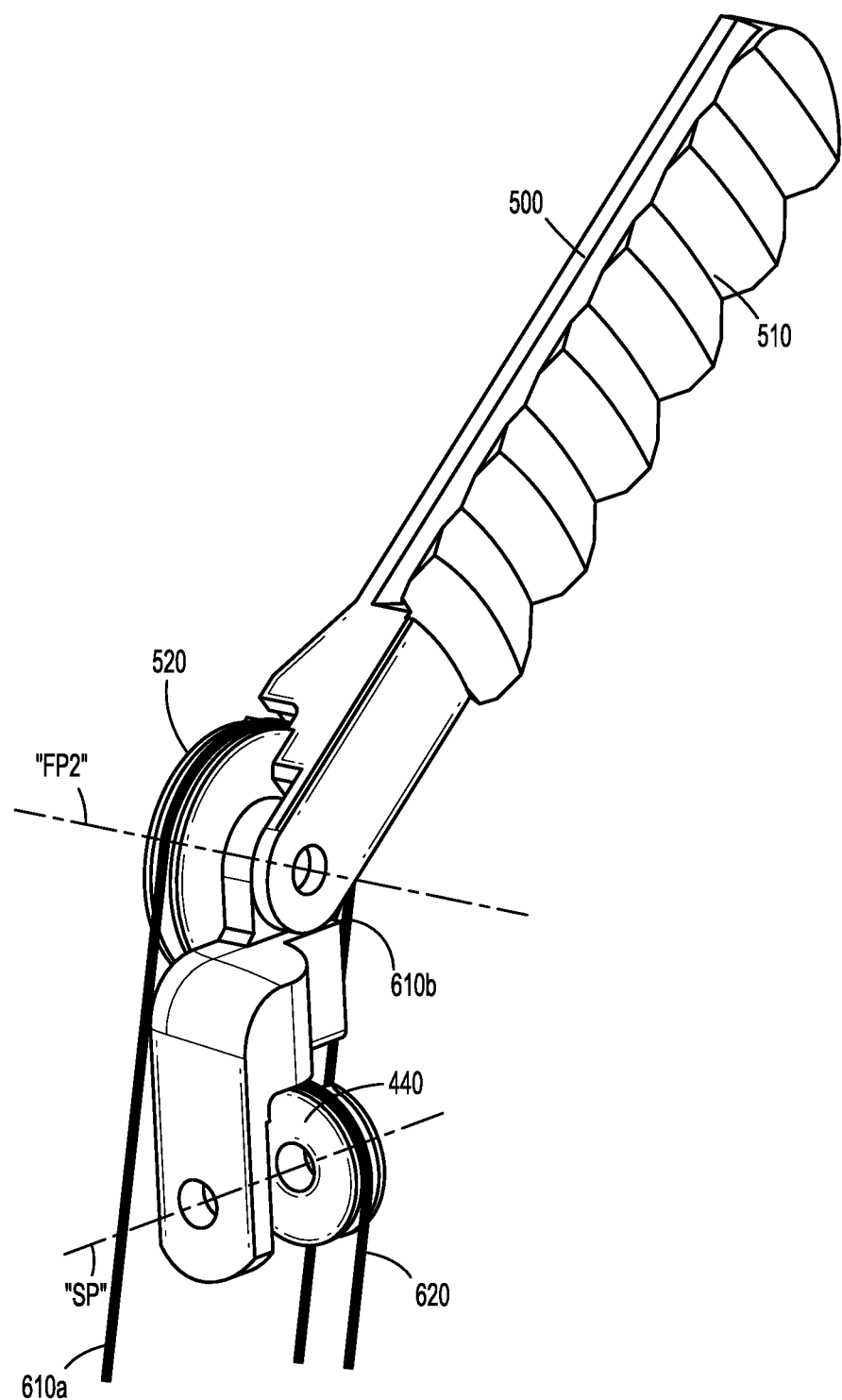
FIG. 4A is a perspective view of one of the jaw members of the surgical device in an open or angled position.

With reference to FIG. 4A, a combination of proximal movement of second grab cable 630 with respect to body portion 200, and relaxation of a first portion 610a and a second portion 610b of second pitch cable 610 causes second jaw member 500 to move in a first direction about the second pulley axis "SP," or common axis "E," and within the first plane "B," e.g., to clamp or dissect tissue. With continued reference to FIG. 4A, a combination of proximal movement of first portion 610a and second portion 610b of second pitch cable 610 (e.g., the same distance) with respect to body portion 200, and relaxation of second grab cable 630 to allow second grab cable 630 to move distally (e.g., the same distance as the proximal movement of first portion 610a and second portion 610b of second pitch cable 610) with respect to body portion 200, causes second jaw member 500 to move in a second direction about the second pulley axis "SP," or common axis "E," and within the first plane "B," e.g., to clamp or dissect tissue.

It is envisioned that cables 600, 610, 620, 630 extend through an elongated part of a surgical instrument and are in mechanical cooperation with knobs, levers, motors and the like to cause pushing/pulling of particular cables. Further, it is envisioned that a powered surgical instrument (or handle assembly thereof) is used to control the movement of cables 600, 610, 620, 630. An example of a powered surgical instrument is described in U.S. Pat. No. 7,931,660 to Aranyi, et al., the entire contents of which being hereby incorporated by reference herein. It is further envisioned that cables 600, 610, 620, 630 are mechanically engaged with controller 40, which is configured to receive commands (e.g., which cables 600, 610, 620, 630 to push/pull) from master station 20. An example of a robotic surgical system utilizing a master station and a controller is shown and described in U.S. Provisional Patent Application Ser. No. 61/914,632, filed on Dec. 11, 2013, the entire content of which is incorporated herein by reference.

Figure 6:
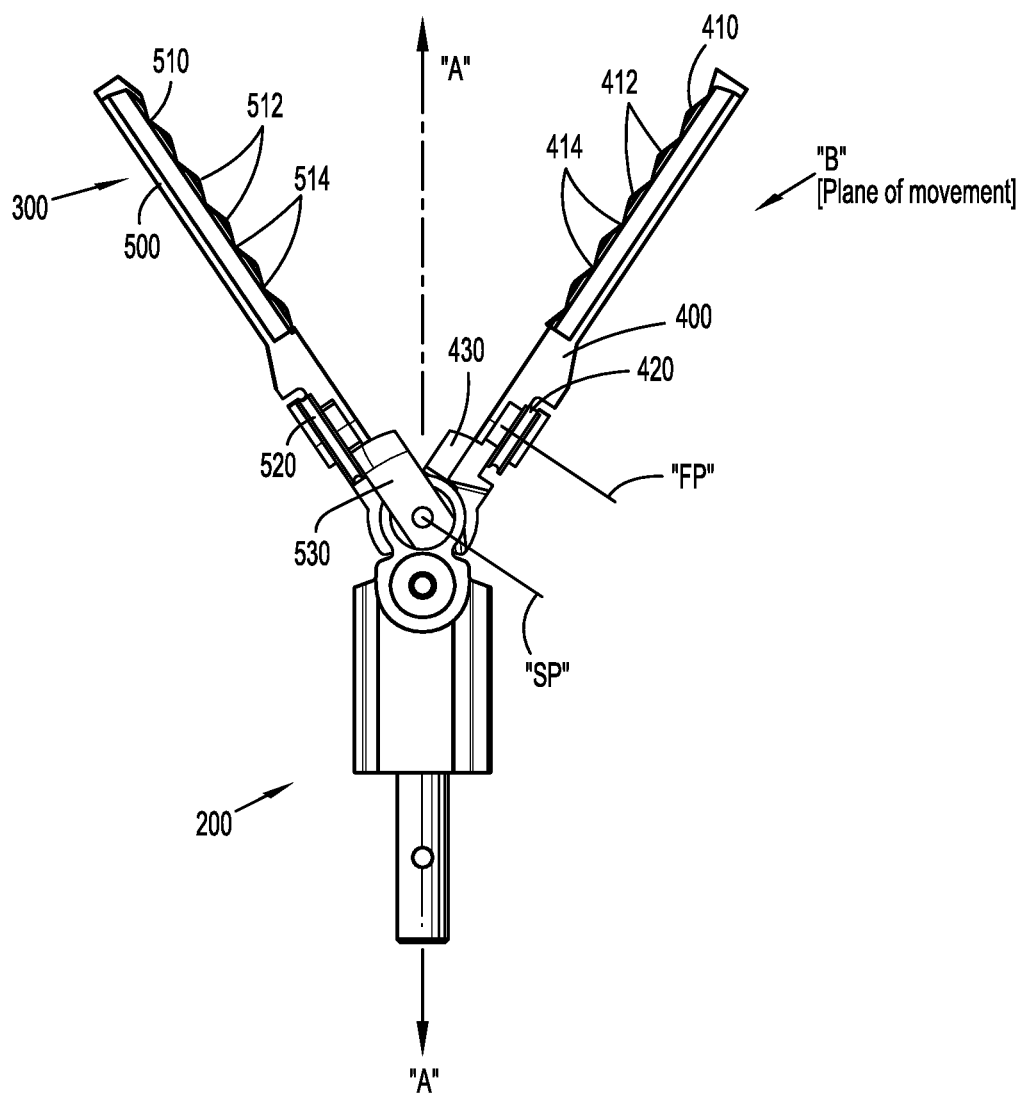
FIG. 6 is a side view of the surgical device of the present disclosure illustrating the jaw members in an open position along the first plane.
Figure 6A:
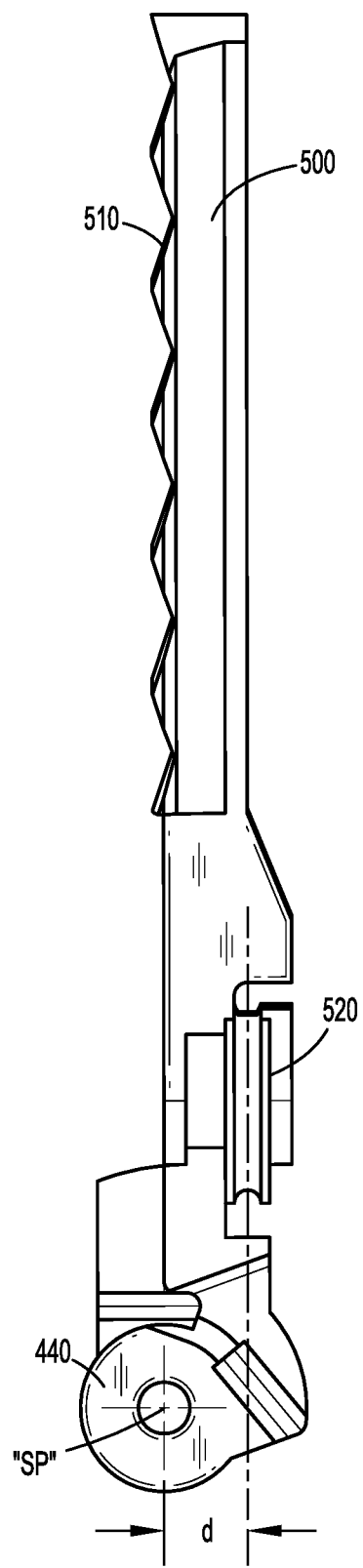
FIG. 6A is a side view of one of the jaw members of the surgical device in a closed position.

In disclosed embodiments of the present disclosure, each idler pulley 450, 460, 550, and 560 has the same diameter as each other, and has the same diameter as each of second pulleys 440 and 540. More particularly, it is envisioned that these diameters are between about 3 mm and about 4 mm (e.g., equal to about 3.78 mm). Additionally, and with reference to FIG. 6A, for example, it is disclosed that the perpendicular distance "d" between the path of second pitch cable 610 about first pulley 520 and the second pulley axis "SP" (about which second pulley 440 rotates) is equal to the diameter of second pulleys 440 and 540. Further, it is disclosed that the perpendicular distance between the path of first pitch cable 600 about first pulley 420 and the second pulley axis "SP" (about which second pulley 540 rotates) is equal to the diameter of second pulleys 440 and 540. Here, it is envisioned that the diameter of second pulleys 440 and 540 is between about 3 mm and about 4 mm (e.g., equal to about 3.78 mm).

It is further envisioned that first pulley 420 of first jaw member 400 and first pulley 520 of second jaw member 500 have different diameters, thus ensuring alignment between idler pulleys 450 and 460 and second pulley 440, and ensuring alignment between idler pulleys 550 and 560 and second pulley 540 (see FIG. 5, for example). Here, it is envisioned that the diameter of first pulley 420 of first jaw member 400 is between about 4 mm and about 5 mm (e.g., equal to about 4.75 mm), and that the diameter of first pulley 520 of second jaw member 500 is between about 6 mm and about 7 mm (e.g., equal to about 6.25 mm)

The present disclosure also relates to methods of using a single surgical device, such as surgical device 100 and/or medical system 10 disclosed herein, to both clamp, shear and dissect tissue depending on the direction the jaw members 400, 500 are moved.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A surgical device, comprising:
a body portion defining a longitudinal axis; and
an end effector disposed adjacent a distal end of the body portion, the end effector including a first jaw member and a second jaw member, wherein at least one jaw member is pivotable with respect to the other jaw member between open and approximated positions along a first plane, wherein each jaw member is independently movable with respect to the other jaw member between a first position where the jaw members are aligned with the longitudinal axis and a second position where at least one jaw member is disposed at an angle with respect to the longitudinal axis and with respect to the first plane, and wherein the at least one jaw member is movable along a second plane through an angle greater than 90 degrees relative to the longitudinal axis and the other jaw member, the second plane transverse to the first plane.

2. The surgical device according to claim 1, wherein each jaw member is pivotable with respect to the other jaw member.

3. The surgical device according to claim 1, wherein each jaw member is independently pivotable with respect to the other jaw member.

4. The surgical device according to claim 1, wherein the first jaw member is movable in the second plane toward its second position, and wherein the second jaw member is movable in the second plane toward its second position.

5. The surgical device according to claim 4, wherein the first jaw member and the second jaw member are concurrently movable in opposite directions from each other within the second plane.

6. The surgical device according to claim 1, wherein in the second position, the jaw members are disposed at an angle with respect to one another.

7. The surgical device of claim 1, wherein in the second position, each jaw member is disposed at an angle with respect to the longitudinal axis and with respect to the first plane.

8. The surgical device of claim 1, wherein the end effector includes a first pulley and a second pulley associated with each jaw member, and wherein rotation of the first pulley causes the respective jaw member to move within the first plane, and wherein rotation of the second pulley causes the respective jaw member to within the second plane.

9. The surgical device of claim 8, wherein the end effector includes four idler pulleys associated with each jaw member, wherein a first set of four idler pulleys is located adjacent a lateral wall of the body portion and is associated with one of the jaw members, and wherein a second set of four idler pulleys is located laterally outward of the first set of four idler pulleys and is associated with the other of the jaw members.

10. The surgical device of claim 8, wherein the end effector includes a first cable associated with the first pulley of the first jaw member, a second cable associated with the second pulley of the first jaw member, a third cable associated with the first pulley of the second jaw member, and a fourth cable associated with the second pulley of the second jaw member, and wherein at least one of proximal and distal movement of a cable results in rotation of its respective pulley.

11. The surgical device of claim 1, wherein the end effector includes a first pulley associated with each jaw member, wherein rotation of the first pulley causes the respective jaw member to move within the first plane, and wherein the first pulley associated with the first jaw member has a different diameter than the first pulley associated with the second jaw member.

12. The surgical device of claim 11, wherein the diameter of the first pulley associated with the first jaw member is between about 3 mm and about 4 mm, and wherein the diameter of the first pulley associated with the second jaw member is between about 6 mm and about 7 mm.

13. A robotic medical system comprising:
a master station including an input device;
a slave station including a surgical instrument, the surgical instrument comprising:
a body portion defining a longitudinal axis; and
an end effector disposed adjacent a distal end of the body portion, the end effector including a first jaw member and a second jaw member, wherein at least one jaw member is pivotable with respect to the other jaw member between open and approximated positions along a first plane, wherein each jaw member is independently movable with respect to the other jaw member between a first position where the jaw members are aligned with the longitudinal axis and a second position where the jaw members are disposed at an angle with respect to the longitudinal axis and with respect to the first plane, and wherein each jaw member is movable along a second plane through an angle greater than 90 degrees relative to the longitudinal axis and the other jaw member, the second plane transverse to the first plane; and
a controller coupled between the master station and the slave station and being configured for receiving a command from the input device and for controlling movement of the surgical instrument.

14. The robotic medical system according to claim 13, wherein each jaw member is independently pivotable with respect to the other jaw member.

15. The robotic medical system to claim 13, wherein the first jaw member is movable in the second plane toward its second position, and wherein the second jaw member is concurrently movable with the first jaw member in an opposite direction from the first jaw member in the second plane toward its second position.

16. The robotic medical system of claim 13, wherein the end effector includes a first pulley and a second pulley associated with each jaw member, and wherein rotation of the first pulley causes the respective jaw member to move within the first plane, and wherein rotation of the second pulley causes the respective jaw member to within the second plane.

* * * * *